United States Patent
Roggy et al.

(10) Patent No.: US 6,183,085 B1
(45) Date of Patent: *Feb. 6, 2001

(54) APPARATUS AND METHOD FOR CONVERTING A STANDARD NON-ROTATABLE DIAGNOSTIC LENS INTO A ROTATABLE DIAGNOSTIC LENS FOR EVALUATION OF VARIOUS PORTIONS OF THE EYE

(76) Inventors: Sheri L. Roggy; David L. Roggy, both of 1643 Langenberg Ave., Iowa City, IA (US) 52240

( * ) Notice: Under 35 U.S.C. 154(b), the term of this patent shall be extended for 0 days.

This patent is subject to a terminal disclaimer.

(21) Appl. No.: 09/193,308

(22) Filed: Nov. 17, 1998

Related U.S. Application Data

(63) Continuation-in-part of application No. 09/022,214, filed on Feb. 11, 1998, now Pat. No. 5,841,510.

(51) Int. Cl.⁷ ........................................ A61B 3/13
(52) U.S. Cl. ............................................. 351/200
(58) Field of Search .................................. 351/200, 205, 351/216–221

(56) References Cited

U.S. PATENT DOCUMENTS

| | | |
|---|---|---|
| 4,033,679 | 7/1977 | Sussman . |
| 4,065,208 | 12/1977 | Currey . |
| 4,134,647 * | 1/1979 | Ramos-Caldera .................. 351/219 |
| 4,568,157 | 2/1986 | Kurwa . |
| 5,255,025 | 10/1993 | Volk . |
| 5,479,222 | 12/1995 | Volk . |
| 5,537,164 | 7/1996 | Smith . |
| 5,589,896 | 12/1996 | Mainster et al. . |
| 5,623,323 * | 4/1997 | Johnson et al. .................. 351/219 |
| 5,652,639 | 7/1997 | Patel et al. . |

OTHER PUBLICATIONS

Brochure of Ocular Instruments, Inc. entitled *Three Mirror Universal Lens*.
Brochure of Ocular Pathology Laboratory II entitled *Retinal Evaluation Utilizing The Three Mirror Fundus Contact Lens*.
Co–pending parent Pat. application Ser. No. 09/022,214, filed Feb. 11, 1998.

* cited by examiner

*Primary Examiner*—George Manuel
(74) *Attorney, Agent, or Firm*—Blackwell Sanders Peper Martin

(57) ABSTRACT

An apparatus and method for converting a non-rotatably diagnostic lens into a rotatable device for evaluation of various portions of the eye wherein the lens device includes a housing member having opposed end portions and associated wall portions, a viewing lens positioned adjacent one end portion of the housing member and at least one mirror or other viewing surface located adjacent thereto, the improvement comprising a groove formed in the outer periphery of the housing member and a peripheral member cooperatively engageable with the groove, the peripheral member being shaped and dimensioned such that the housing member is rotatably movable relative to the peripheral member when the peripheral member is engaged with the groove. This arrangement enables a user to hold the peripheral member stationary and thereafter rotate the entire lens device so as to selectively position the at least one mirror or other viewing surface at the appropriate eye location for ocular evaluation. Preferably, the housing member is rotatable a full 360° while the peripheral member remains stationary within a users grasp. Several alternative embodiments for rotatably engaging a peripheral member to the housing member of a lens device are disclosed. Although the present invention is particularly adaptable for use in association with a wide variety of diagnostic lenses such as gonioscopy and/or fundoscopic lenses, the present invention is likewise equally adaptable for use in many other eye lens applications including lenses used in laser treatment and/or surgery of the eye.

24 Claims, 3 Drawing Sheets

APPARATUS AND METHOD FOR CONVERTING A STANDARD NON-ROTATABLE DIAGNOSTIC LENS INTO A ROTATABLE DIAGNOSTIC LENS FOR EVALUATION OF VARIOUS PORTIONS OF THE EYE

This application is a continuation-in-part of application Ser. No. 09/022,214, filed Feb. 11, 1998, now U.S. Pat. No. 5,841,510, entitled Rotatable Diagnostic Lens For Evaluation Of The Irido-Corneal Angle, Retina And Other Portions Of The Eye.

FIELD OF THE INVENTION

The present invention relates generally to diagnostic lens devices for examining portions of the human eye and, more particularly, to an apparatus and method for converting a standard diagnostic lens housing any number of mirrors such as a gonioscopy lens or a fundus contact lens used for both irido-corneal and retinal evaluations as well as evaluation of other portions of the eye into a rotatable diagnostic lens wherein the mirror/mirrors associated with the lens device can be selectively rotated to properly position the appropriate mirror opposite the area of the eye to be examined.

BACKGROUND OF THE INVENTION

Diagnostic lenses such as fundoscopic and gonioscopy lenses are commonly used for various types of ocular evaluation. These types of lenses are specifically designed to allow different areas of the retina and other portions of the eye to be evaluated and are typically used to review the posterior, equatorial and anterior areas of the retina, the ora serrata, the anterior chamber, the posterior chamber, the vitreous chamber, and more. Such lenses are useful because they allow an optometrist, ophthalmologist, or other eye care professional to examine the interior of the eye for potential ocular defects and/or disease. Because the pupil of the eye is small and the eye is essentially spherical, it is difficult to visually examine various interior portions of the eye with a normal lens. Thus, it is difficult to examine many portions of the eye such as peripheral portions of the vitreous chamber and the retina. In order to allow viewing of substantially the entire vitreous chamber and retina of the eye, as well as other areas, diagnostic lenses such as gonioscopy lenses and fundus contact lenses were developed.

Known prior art diagnostic lenses, such as the known gonioscopy lenses and multi-mirrored fundus contact lenses, typically include a concave central lens located at one end portion thereof and a plurality of mirrors positioned around the central lens which are encased in a funnel-shaped cone and protected by a planar glass viewing surface. The central viewing lens is utilized to assess the posterior 30° of the retina. Lateral or adjacent to the central lens are a plurality of mirrors, typically three mirrors, which are spaced 120° apart and are mounted at different angles of inclination to the funnel-shaped cone to allow different areas of the eye to be evaluated. Typically, these mirrors are angled at 59°, 67° and 73°. These mirrors reflect light at different angles so that different parts of the eye can be examined. In order to identify a specific mirror, manufacturers of these lenses have universally assigned three sizes and shapes to the mirrors so that the users thereof can quickly and easily identify each mirror and its associated angular inclination.

Other prior art diagnostic lenses of this type are formed from a solid piece of clear plastic of a specific polymer or acrylic resin composition wherein surfaces are shaped and cut at different angles of inclination such that the natural refraction of light through these angled surfaces will likewise allow different parts of the eye to be examined. These cut and angled surfaces function in the same manner as the mirrors described above and such surfaces are also differently sized and shaped for easy identification.

The selection and position of the specific mirror or angled surface to be utilized during an evaluation depends upon that portion of the eye which needs to be evaluated. The selected mirror or surface is then placed opposite the area to be evaluated. For example, if the 12 o'clock position of the peripheral retina needs to be evaluated and a mirrored lens is being utilized, the median sized mirror which is angled at 67° can be positioned at the 6 o'clock position of the retina so as to view the affected area. Each mirror or angled surface allows the user to inspect and evaluate different portions of the eye based upon the shape and inclination of such mirrors or angled surfaces.

Because the mirrors or surfaces are inclined at different angles and are typically circumferentially spaced apart, it is necessary to rotate the known prior art lenses a full 360° in order to examine the entire retina or other portions of the eye. Manipulation and positioning of the appropriate mirror or surface at the appropriate location relative to the retina is generally accomplished by manually rotating the entire lens device on the eye of the patient until the selected mirror or surface is located in the proper position. This orientation is obtained by simply rotating the lens between the forefinger and thumb of the user so that the lens is 180° opposite the area to be evaluated. Rotation of the lens can be accomplished with one or two hands depending upon the practitioner. The user, when using a prior art lens of this type, must therefore coordinate the use and manipulation of the slit-lamp biomicroscope which is used in conjunction with these types of lenses with manual rotation of the gonioscopy or other diagnostic lens on the eye of the patient.

Although co-pending U.S. patent application Ser. No. 09/022,214, now U.S. Pat. No. 5,841,510, is directed to several embodiments of a rotatable diagnostic lens for ocular evaluation wherein any number of mirrors associated with such lens devices can be rotated separate and apart from the overall device, it is also desirable to provide an apparatus and method for converting existing conventional non-rotatable diagnostic lens to a rotatable type lens which will enable a user to not only continue to use existing lens equipment, but which will enable the user to more easily and freely manipulate the mirrors associated with such lens during ocular evaluations.

SUMMARY OF THE INVENTION

The present invention teaches the construction and operation of several embodiments of an apparatus and method for converting a non-rotatable diagnostic lens for ocular evaluation into a rotatable lens device. More particularly, in one aspect of the present invention, an annular peripheral member or jacket is rotatably positioned and/or installed adjacent the outer periphery of the housing member of a conventional non-rotatable diagnostic lens intermediate the opposed end portions thereof, both the annular peripheral member and the lens device being rotatably movable relative to each other when the annular peripheral member is engaged therewith. This arrangement enables a user to hold the annular peripheral member in a fixed stationary position while the conventional lens device is selectively rotated therewithin to properly orient the appropriate mirror/mirrors or angled surfaces associated with such lens device for viewing of the desired area of the eye. With the present annular peripheral member or jacket properly installed, a conventional diagnostic lens can be rotated a full 360° allowing continuous or uninterrupted viewing of the interior portions of the eye when the diagnostic lens is positioned adjacent a patient's eye for ocular evaluation. The eye practitioner can therefore securely hold the diagnostic lens within the present attachment member by simply holding the peripheral member between the thumb and forefinger and thereafter rotating the entire diagnostic lens device through the use of one's index finger. Unlike the lens devices disclosed in the parent application, now U.S. Pat. No. 5,841,510, use of the present peripheral member does allow the diagnostic lens to rotate or otherwise move while the lens device is positioned in contact with a patient's eye. As with the conventional use of diagnostic lens such as known gonioscopy lens and multi-mirror fundus contact lens, a cushioning agent is used between the lens device and a patient's eye to substantially reduce and/or eliminate any discomfort to the patient during the mirror/angled surface selection and positioning process. Also, importantly, use of the present attachment device enables rotation of the lens device to be easily accomplished with one hand.

It is recognized and anticipated that a wide variety of different constructions can be utilized to rotatably mount the present peripheral member in proper position about the housing member of the particular diagnostic lens. For example, in one embodiment of the present invention, an annular groove or channel can be formed within the wall means associated with the housing member of a typical diagnostic lens, and the peripheral member of the present invention may include any plurality of set screws or other inwardly projecting members which are sized and shaped for cooperative engagement with the groove or channel. When the terminal end portions of the respective set screws or other projections are positioned within the groove or channel formed within the housing wall portion of the diagnostic lens, the set screws or other projections will prohibit up and down movement of the present peripheral member relative to the diagnostic lens and, at the same time, will allow rotatable movement of both members relative to each other as previously explained.

It is also recognized and anticipated that a wide variety of other male/female connector arrangements may also be utilized in this particular application and still other mechanical arrangements may likewise be utilized in association with the peripheral member and the diagnostic lens without departing from the spirit and scope of the present invention. For example, small beads or other projections can be circumferentially spaced around the inner wall of the annular peripheral member such that the peripheral member can be slidably moved along the outer periphery of the diagnostic lens until such projections cooperatively engage the annular groove or channel. Several alternative embodiments for rotatably engaging a peripheral member to the housing member of a lens device are disclosed herein. Regardless of the specific mechanical construction, the mirror/mirrors or angled surfaces associated with a particular diagnostic lens device are selectively rotatable relative to the patient's eye by simply holding the present peripheral member stationary and rotating the diagnostic lens relative thereto.

Although the present invention is particularly adaptable for use in association with a wide variety of diagnostic lenses such as gonioscopy and/or fundus contact type lenses, the present invention is likewise equally adaptable for use in many other eye lens applications including other types of ophthalmological lenses as well as lenses used in laser treatment and/or surgery of the eye.

It is therefore an object of the present invention to provide means for converting a non-rotatable diagnostic lens into a rotatable diagnostic lens.

Another object is to provide means for facilitating the proper orientation of a diagnostic and/or treatment type lens device for both ocular evaluation and treatment purposes while the lens device is positioned adjacent a patient's eye.

Other objects and advantages of the present invention will become apparent to those skilled in the art after considering the following detailed specification which discloses several representative embodiments of the present attachment mechanism in conjunction with the accompanying drawings wherein:

DETAILED DESCRIPTION OF THE PRESENT INVENTION

Figure 1:
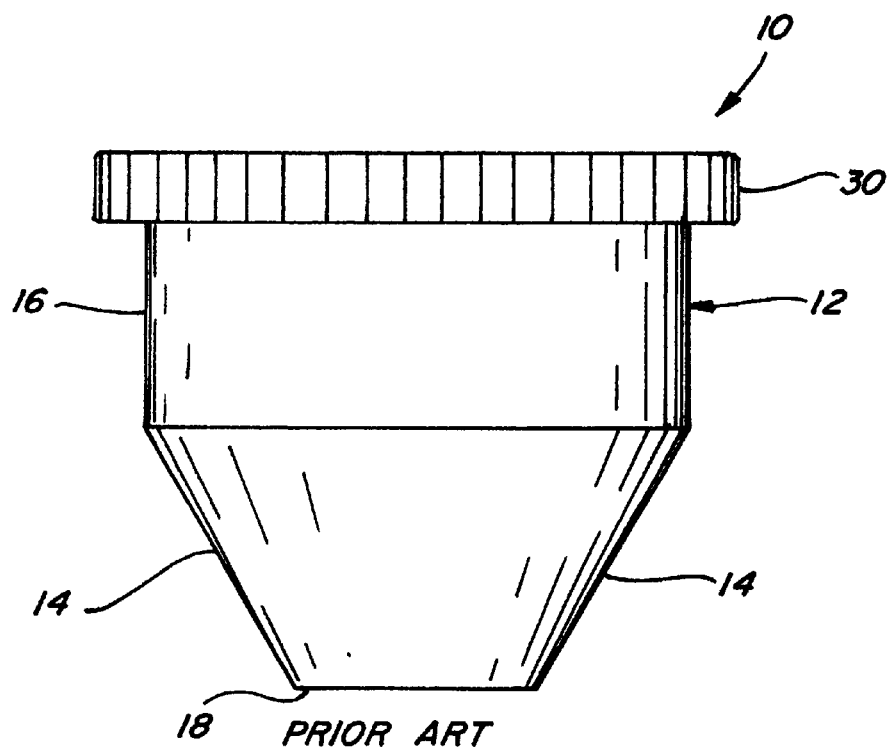
FIG. 1 is a side elevational view of a typical prior art lens device.
Figure 2:
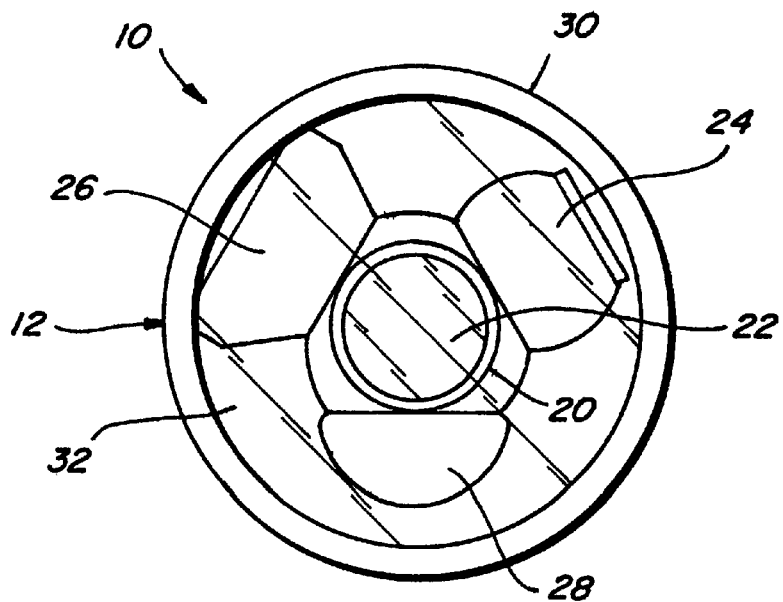
FIG. 2 is a top plan view of the lens device of FIG. 1 showing the fixed central viewing lens and three mirrors located adjacent thereto in association therewith.
Figure 4:
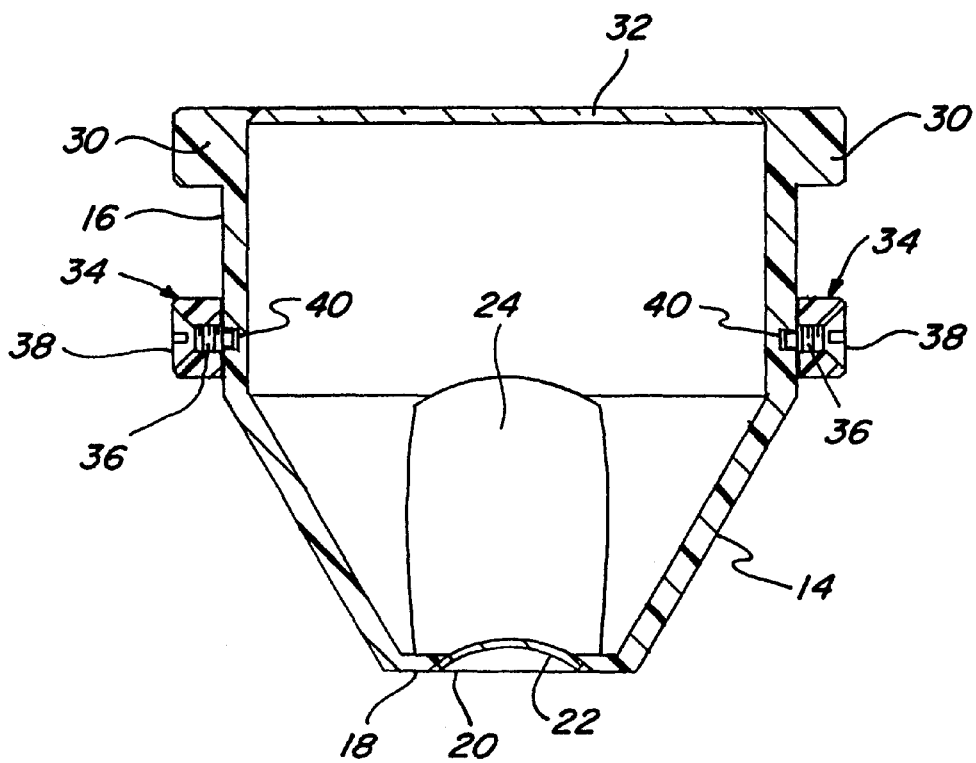
FIG. 4 is a cross-sectional view of the lens device of FIG. 3 taken along line 4—4 thereof.

Referring to the drawings more particularly by reference numbers wherein like numerals refer to like parts, number 10 in FIGS. 1 and 2 identifies a typical diagnostic or treatment lens commonly used for various types of ocular evaluation. The lens 10 includes a housing member 12 as best shown in FIG. 1 which is substantially hollow and is defined by annular wall portions 14 and 16. Wall portion 14 is substantially frusto-conical in shape and includes an annular end wall portion 18 adjacent one end portion thereof defining an opening 20 (FIGS. 2 and 4) therethrough into which a fixed central lens 22 is mounted. The central lens 22 is generally concave in shape as illustrated in FIGS. 2 and 4 and is typically fixedly mounted to the end wall portion 18 by means well known in the art. Central lens 22 is positioned adjacent to a patient's eye and is utilized to view and assess the posterior 30° of the retina including the disc, arcades and macula. A plurality of mirrors 24, 26 and 28 positioned adjacent the central viewing lens 22 as will be hereinafter explained are utilized in conjunction with central lens 22 to view other interior portions of the eye including, but not limited to, the irido-corneal angle and peripheral portions of the vitreous chamber and the retina. The concavity of the central lens 22 allows for magnification of the interior structure of the eye, especially the irido-corneal angle and the retina, and although the lens 22 is generally of a circular construction, other shapes and configurations including a substantially flat shape are also utilized.

Figure 3:
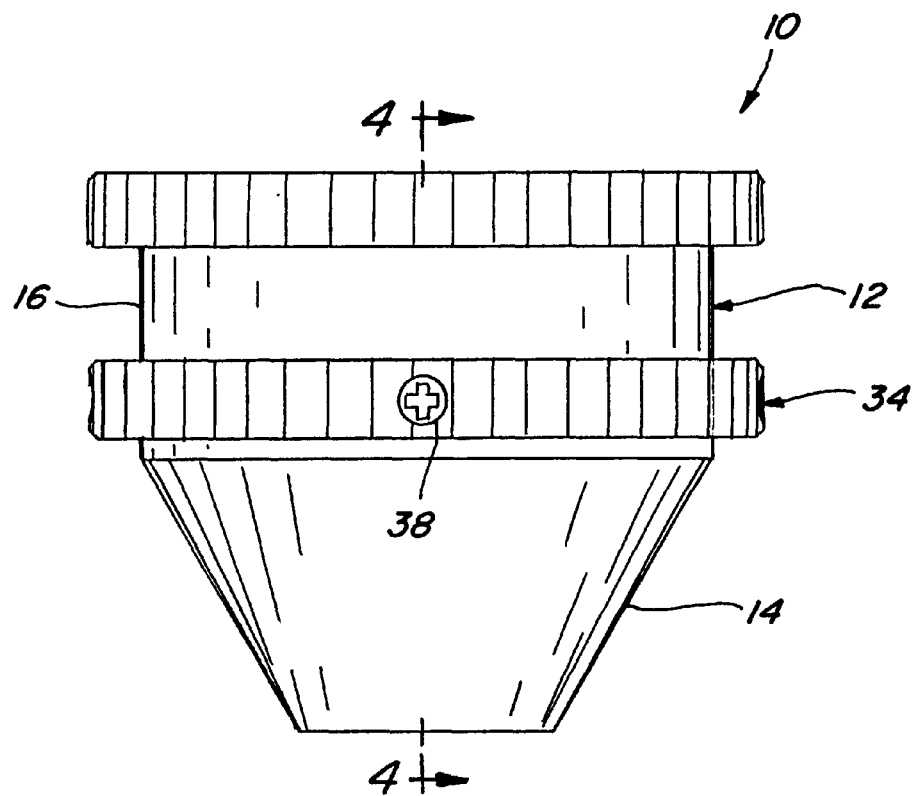
FIG. 3 is a side elevational view of the present peripheral member attached to the prior art lens device of FIG. 1, the peripheral member being constructed in accordance with the teachings of the present invention.

The wall portion 16 of housing member 12 is substantially cylindrical in shape (FIGS. 1 and 3) and is typically integrally formed with wall portion 14. Wall portion 16 also typically further includes an annular lip or flange portion 30 adjacent the upper end portion thereof as best illustrated in FIGS. 1 and 3 so as to allow a user to more easily hold the device 10 in a fixed position adjacent the patient's eye. A transparent planar viewing member 32 is fixedly secured adjacent the top edge portion of either wall portion 16 or annular flange portion 30 as best shown in FIGS. 2 and 4, the member 32 being made of glass or some other suitable viewing material. In this regard, the member 32 can be either clear or filtered depending upon the particular use of the device 10 as some laser applications require a filtered viewing member 32. It is also recognized that the housing member 12 may take on other shapes and configurations as compared to wall portions 14 and 16 disclosed in FIGS. 1, 3 and 4 without departing from the spirit and scope of the present invention.

Although some of the known diagnostic and/or treatment lenses commonly used for both ocular evaluation and surgery may include any plurality of mirrors, for illustrative purposes only, the present construction will be described and disclosed with respect to a three mirror arrangement similar to the mirror arrangement associated with known three fundus contact lenses presently in use. In this regard, as illustrated in FIG. 2, the mirrors 24, 26 and 28 are typically circumferentially spaced adjacent annular end portion 18 such that the mirrors are angularly inclined relative to the vertical adjacent the central lens 22. In the case of the three mirrors illustrated in FIG. 2, such mirrors are circumferentially spaced 120° apart and are mounted at different angles of inclination relative to the frusto-conical shaped wall portion 14 so as to allow the irido-corneal angle and different areas of the retina or other portions of the eye to be evaluated. As previously explained, typically, the mirrors 24, 26 and 28 are inclined at angles such as 59°, 67° and 73° relative to the vertical such that each respective mirror will reflect light at a different angle so that different parts of the eye can be examined. In the case of the known three mirror fundus contact lenses, manufacturers of these types of lenses have universally assigned different sizes and shapes to each such mirror so that users can quickly and easily identify each mirror and its associated angular inclination. The means for mounting the respective mirrors within the housing member 12 are well known in the art and any suitable means can be utilized to accomplish this task.

The present invention includes an annular peripheral member or jacket 34 which is shaped and dimensioned so as to be rotatably positioned and/or mounted adjacent the outer periphery of housing member 12 intermediate the opposed end portions thereof as best illustrated in FIGS. 3 and 4. In the particular embodiment illustrated in FIGS. 3 and 4, the member 34 is substantially cylindrical in shape so as to be rotatably mounted to the wall portion 16 of lens device 10. In this regard, the annular member 34 includes at least one opening 36, and preferably a plurality of spaced openings 36, as best shown in FIG. 4 adaptable for receiving a partially threaded pin member or set screw 38. In order to mount the peripheral member 34 to the housing member 12 of a typical lens device 10, a groove or recess 40 is positioned and located on wall portion 16 at a selected location therealong, the groove or recess 40 being preferably formed completely around the periphery of wall portion 16 and being sized and shaped so as to receive the terminal end portion of pin members 38 as will be hereinafter explained. Once the groove or recess 40 is formed, the threaded pin members 38 are thereafter inserted within the plurality of openings 36 such that the terminal end portions of each respective pin member 38 extends into the groove or recess 40 formed within the wall portion 16. When so engaged, the pin members 38 will prohibit up and down movement of the peripheral member or jacket 34 relative to the housing member 12 and, at the same time, will allow rotational movement of member 12 relative to member 34. Rotation of lens device 10 is accomplished by simply holding the peripheral member 34 stationary such as by gripping the same between the thumb and forefinger and thereafter rotating the entire lens device 10 through the use of one's index finger so as to properly align and orient the appropriate mirror at the appropriate location opposite the area of the retina or other eye portion to be evaluated. A user can simply rotate the wall portion 14 or 16 of lens device 10 while holding the peripheral member 34 in a fixed stationary position so that the selected mirror is properly positioned adjacent the eye of the patient. This rotation can be easily accomplished with one hand.

As a result, a conventional diagnostic lens such as the lens device 10 can be easily converted into a rotatable lens device by merely forming the groove or recess 40 within a wall portion of the housing member 12 and thereafter attaching the peripheral member 34 as previously explained. In this regard, depending upon the construction and configuration of the housing member associated with a particular diagnostic lens such as the housing member 12, it is recognized and anticipated that the peripheral member or jacket 34 can be rotatably mounted to any particular wall portion associated with the housing member 12 including the frusto-conical shaped portion 14 illustrated in FIGS. 1 and 3, if so desired. In this eventuality, both the size and shape of the groove or recess formed within wall portion 14 as well as the length of the respective pin members 38 should be such so as to accommodate rotational movement between the peripheral member 34 and the wall portion 14. It is also recognized and anticipated that the peripheral member 34 as well as the groove 40 may be constructed so as to only extend partially around the periphery of the wall means associated with housing member 12.

Figure 5:
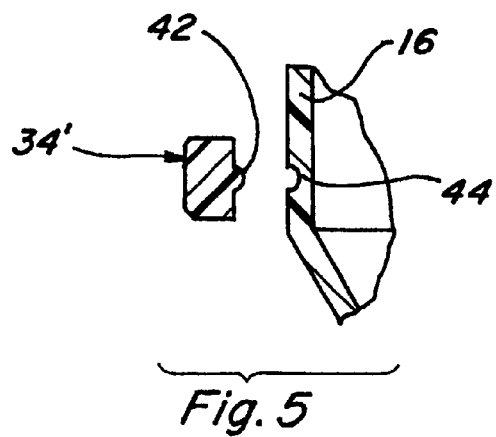
FIG. 5 is a partial cross-sectional view showing an alternative embodiment for rotatably attaching the peripheral member of the present invention to the housing member of a lens device.

FIG. 5 discloses another engagement arrangement between member 34' and wall portion 16 for achieving 360° rotatability of a particular lens device 10 relative to the peripheral member or jacket 34'. In the embodiment illustrated in FIG. 5, the peripheral member 34' may include any number of projections 42 which are preferably integrally formed with the member 34' and a corresponding groove or recess 44 is formed within the wall portion 16. In this particular arrangement, the projections 42 are constructed so as to move or otherwise slide along the outer surface of housing member 12 as the member 34' is being positioned thereon until the projections 42 engage the groove 44. In this regard, the groove 44 is cooperatively formed so as to receive and cooperatively engage the projections 42 when inserted therewithin such that the projections 42 will remain engaged with the groove 44 and, at the same time, such cooperative engagement will allow rotational movement of the particular lens device 10 relative to the peripheral member 34' as previously explained. Here again, the projections 42 and the groove 44 can take on any configuration so long as the annular member 34' remains rotatably engaged with the groove 44. It is also recognized and anticipated that any number of projections 42 can be utilized around the inner periphery of the member 34' including use of a single elongated projection which may extend circumferentially along and around the outer periphery of the housing member a sufficient distance to achieve the stated objective.

Figure 6:
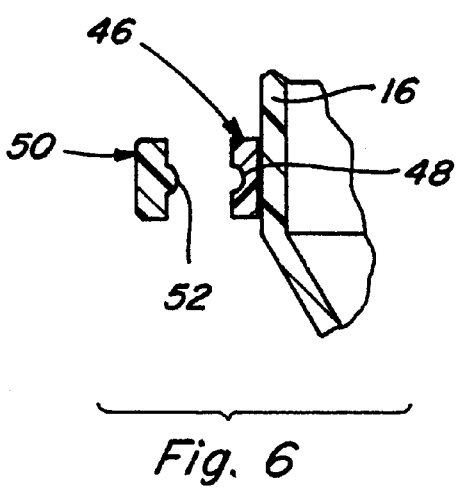
FIGS. 6 and 7 are partial cross-sectional views showing still other embodiments of the present peripheral member.

FIG. 6 illustrates still another constructional arrangement for rotatably engaging a peripheral member to the housing member 12 of a typical lens device 10. In this particular embodiment, a pair of peripheral members 46 and 50 are utilized to accomplish the present task, the peripheral member 46 being sized and shaped so as to be adhesively or otherwise fixedly attached to the housing member 12 such as adjacent wall portion 16. The peripheral member 46 includes a recess or groove 48 formed therein for cooperatively receiving and engaging at least one correspondingly shaped projection 52, and preferably a plurality of spaced projections 52, associated with a second peripheral member 50. Like the engagement arrangement associated with peripheral members 34 and 34' illustrated in FIGS. 3–5, with peripheral member 46 fixedly attached to housing member 12 and peripheral member 50 cooperatively engaged with member 46, the projections 52 will likewise extend into the groove 48 and the members 46 and 50 will freely rotate relative to each other. This particular arrangement obviates the need for forming a groove or recess in the housing member 12 such as the grooves 40 and 44 illustrated in FIGS. 4 and 5 but, at the same time, likewise allows rotational movement of the lens device 10 relative to the peripheral member 50 as previously explained.

Figure 7:
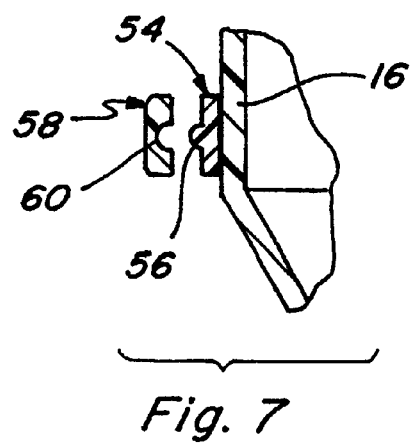

It is also recognized and anticipated that the construction and location of the mating male and female connections 38/40, 42/44 and 48/52 can all be reversed so that those portions located on one member can be located on the other member and vice versa without departing from the spirit and scope of the present invention. For example, in the embodiment disclosed in FIG. 6, it is recognized that the male and female portions 48/52 associated with members 46 and 50 can be reversed as illustrated in FIG. 7. In the FIG. 7 embodiment, the peripheral member 54 which is adhesively or otherwise fixedly attached to the wall portion 16 of lens device 10 includes at least one projection 56, and preferably a plurality of spaced projections 56, which are sized and shaped to cooperatively receive and engage a corresponding groove or recess 60 formed in peripheral member 58. In all other respects, the operation and rotatability of the members 54 and 58 relative to each other is substantially similar to the operation and rotatability of the members 46 and 50 previously described with respect to FIG. 6.

It is also recognized and anticipated that a wide variety of other male/female connection means may be used in association with rotatably attaching the members 34, 34', 46 and 54 to the housing member 12 without departing from the spirit and scope of the present invention. For example, the members 46 and 54 could form a bracket type member which would easily attach or otherwise clamp to existing landmarks or portions of the outer surface of the particular lens device being modified. Still other constructions and configurations of the members 34, 34', 46, 50, 54 and 58 are likewise envisioned and anticipated.

It is also recognized that all of the embodiments of the present invention are likewise adaptable for use with those known diagnostic and/or treatment lenses formed from a solid piece of clear plastic or some other specific polymeric or acrylic resin composition wherein the mirrors 24, 26 and 28 illustrated in FIG. 2 are replaced by angled surfaces formed or otherwise cut into the solid member. In these types of lens, the central lens 22 and the transparent viewing member 32 are formed directly into the top and bottom surfaces of the solid member and the angled surfaces function in the same fashion as previously described above with respect to mirrors 24, 26 and 28. The peripheral members 34, 34', 50 and 58 will rotate and attach to the solid member forming this type of lens device in the same manner as described above with respect to FIGS. 3–7.

Although the various embodiments of the present invention are particularly adaptable for use in association with a wide variety of diagnostic type lenses such as gonioscopy and fundoscopic lenses, the present invention is likewise equally adaptable for use in many other eye lens applications including other types of ophthalmological lenses as well as lenses used in laser treatment and/or surgery of the eye. In this regard, regardless of the specific use, the present invention can be used in association with any of a variety of standard diagnostic or treatment procedures that involve the use of a diagnostic or treatment type ocular lens. In addition, the peripheral members 34, 34', 46, 50, 54 and 58 can be made from a wide variety of different types of materials including metal, metal alloys and plastics as well as any various combinations of such materials. Still further, the overall shape and dimensions of the members 34, 34', 46, 50, 54 and 58 can be varied to accommodate the particular lens device to which they will be rotatably attached.

In addition, although it is preferred that the peripheral members 34, 34', 50 and 58 rotate a full 360° relative to the housing member 12 of a particular lens device 10, it is likewise recognized and anticipated that the construction of the members 34, 34', 46, 50, 54, 58 and the recess or groove 40 can be such that the rotatable mounting of the such members to the housing member 12 will provide for an operative range of rotation of the lens device 10 of less than 360°. In this regard, the range of rotation can vary depending upon the specific use or application of the particular lens device.

Thus, there has been shown and described several embodiments of an apparatus and method for converting a non-rotatable lens device to a rotatable device, which apparatus and methods fulfill all of the objects and advantages sought therefor. Many changes, modifications, variations and other uses and applications of the present constructions will, however, become apparent to those skilled in the art after considering this specification and the accompanying drawings. All such changes, modifications, variations and other uses and applications which do not depart from the spirit and scope of the invention are deemed to be covered by the invention which is limited only by the claims which follow.

What is claimed is:

1. In a lens device for examining portions of the human eye including a housing member having opposed end portions and associated wall means, the housing member having a viewing lens positioned adjacent one end portion thereof and at least one mirror located adjacent the viewing lens, the improvement comprising a groove formed in the wall means associated with the housing member, and a peripheral member cooperatively engageable with said groove, said peripheral member being shaped and dimensioned such that the housing member is rotatably movable relative to said peripheral member when said peripheral member is engaged with said groove such that the at least one mirror is selectively positionable relative to a portion of the human eye to be examined.

2. The improvement defined in claim 1 wherein said peripheral member includes at least one opening extending therethrough, and at least one pin member insertably receivable within said at least one opening and positionable within said groove when said peripheral member is positioned adjacent the outer periphery of the housing member.

3. The improvement defined in claim 1 wherein said peripheral member includes a plurality of openings extending therethrough, and a plurality of pin members insertably receivable within the respective openings and each positionable within said groove when said peripheral member is positioned adjacent the outer periphery of the housing member.

4. The improvement defined in claim 1 wherein said peripheral member includes at least one projection, said at least one projection being shaped and dimensioned so as to be insertably receivable with said groove when said peripheral member is positioned adjacent the outer periphery of the housing member.

5. The improvement defined in claim 1 wherein said peripheral member includes a plurality of projections, each of said projections being shaped and dimensioned so as to be insertably receivable within said groove when said peripheral member is positioned adjacent the outer periphery of the housing member.

6. The improvement defined in claim 1 wherein the housing member has a transparent planer viewing member associated with one end portion thereof.

7. The improvement defined in claim 1 including a plurality of mirrors located adjacent the viewing lens.

8. The improvement defined in claim 1 wherein the housing member includes a frusto-conical shaped portion.

9. The improvement defined in claim 1 wherein the housing member includes a substantially cylindrical portion.

10. The improvement defined in claim 1 wherein the housing member is rotatable a full 360°.

11. In a lens device for examining portions of the human eye including a housing member having opposed end portions and associated wall means, the housing member having a viewing lens positioned adjacent one end portion thereof and at least one mirror located adjacent the viewing lens, the improvement comprising first and second cooperatively engageable peripheral members, said first peripheral member being fixedly attached to the wall means associated with the housing member, said first peripheral member being rotatably moveable relative to said second peripheral member when engaged therewith such that when said first peripheral member is fixedly attached to the housing member the at least one mirror is selectively positionable relative to a portion of the human eye to be examined.

12. The improvement defined in claim 11 wherein said first peripheral member includes a groove formed therein, and said second peripheral member includes at least one projection insertably receivable within said groove so as to allow relative rotational movement between said first and second peripheral members.

13. The improvement defined in claim 12 wherein said second peripheral member includes a plurality of projections, each of said projections being insertably receivable within said groove so as to allow relative rotational movement between said first and second peripheral members.

14. The improvement defined in claim 11 wherein said first peripheral member includes at least one projection, and said second peripheral member includes a groove formed therein, said at least one projection being insertably receivable within said groove so as to allow relative rotational movement between said first and second peripheral members.

15. The improvement defined in claim 14 wherein said first peripheral member includes a plurality of projections, each of said projections being insertably receivable within said groove so as to allow relative rotational movement between said first and second peripheral members.

16. The improvement defined in claim 11 wherein the housing member is rotatable a full 360°.

17. A method of converting a lens device for examining portions of the human eye into a rotatable device wherein the lens device includes a housing member having opposed end portions and associated wall means, the housing member having a viewing lens positioned adjacent one end portion thereof and at least one mirror located adjacent the viewing lens, said method comprising the following steps:

(a) forming a groove in the wall means associated with the housing member intermediate the opposed end portions thereof, (b) providing a peripheral member which is cooperatively engageable with said groove, said peripheral member being shaped and dimension such that the housing member is rotatably moveable relative to said peripheral member when said peripheral member is engaged with said groove; and (c) engaging said peripheral member with said groove such that the housing member can be rotatably moved relative to said peripheral member to selectively position the at least one mirror relative to a portion of the human eye to be examined.

18. A method of converting a lens device for examining portions of the human eye into a rotatable device wherein the lens device includes a housing member having opposed end portions and associated wall means, the housing member having a viewing lens positioned adjacent one end portion thereof and at least one mirror located adjacent the viewing lens, said method comprising the following steps:

(a) providing first and second cooperatively engageable peripheral members, said first peripheral member being rotatably moveable relative to said second peripheral member when engaged therewith;

(b) fixedly attaching said first peripheral member to the wall means associated with the housing member; and (c) engaging said second peripheral member to said first peripheral member such that the housing member can be rotatably moved relative to said second peripheral member to selectively position the at least one mirror relative to a portion of the human eye to be examined.

19. The method defined in claim 18 wherein said first peripheral member includes a groove formed therein, and said second peripheral member includes at least one projection insertably receivable within said groove so as to allow relative rotational movement between said first and second peripheral members.

20. The method defined in claim 18 wherein said first peripheral member includes at least one projection, and said second peripheral member includes a groove formed therein, said at least one projection being insertably receivable within said groove so as to allow relative rotational movement between said first and second peripheral members.

21. A lens device for examining portions of the human eye comprising a housing member having opposed end portions and associated wall means, said housing member having a viewing lens positioned adjacent one end portion thereof and having at least one mirror located adjacent said viewing lens, said housing member further including a groove formed in its associated wall means intermediate the opposed end portions thereof, and a peripheral member cooperatively engageable with said groove, said housing member being rotatably movable relative to said peripheral member such that the at least one mirror is selectively positionable relative to a portion of the human eye to be examined.

22. A lens device for examining portions of the human eye comprising a housing member having opposed end portions and associated wall means, said housing member having a viewing lens positioned adjacent one end portion thereof and having at least one mirror located adjacent said viewing lens, and first and second cooperatively engageable peripheral members, said first peripheral member being fixedly attached to the wall means associated with said housing member, said first peripheral member being rotatably moveable relative to said second peripheral member when engaged therewith such that the at least one mirror is selectively positionable relative to a portion of the human eye to be examined.

23. In a lens device for examining portions of the human eye including a member having opposed end portions and associated wall means, the member having at least one surface located adjacent to one of the opposed end portions for viewing portions of the eye, the improvement comprising a groove formed in the wall means associated with the member, and a peripheral member cooperatively engageable with said groove, said peripheral member being shaped and dimensioned such that the member is rotatably movable relative to said peripheral member when said peripheral member is engaged with said groove such that the at least one surface is selectively positionable relative to a portion of the human eye to be examined.

24. In a lens device for examining portions of the human eye including a member having opposed end portions and associated wall means, the member having at least one surface located adjacent to one of the opposed end portions for viewing portions of the eye, the improvement comprising first and second cooperatively engageable peripheral members, said first peripheral member being fixedly attached to the wall means associated with the member, said first peripheral member being rotatably moveable relative to said second peripheral member when engaged therewith such that when said first peripheral member is fixedly attached to the member the at least one surface is selectively positionable relative to a portion of the human eye to be examined.

* * * * *